United States Patent [19]

Sugimori et al.

[11] Patent Number: 4,534,883

[45] Date of Patent: Aug. 13, 1985

[54] 4-UNSUBSTITUTED OR SUBSTITUTED-4 CYANOTERCYCLOHEXANE DERIVATIVES

[75] Inventors: Shigeru Sugimori, Fujisawashi; Tetsuhiko Kojima, Yokohamashi; Toyoshiro Isoyama, Yokohamashi; Kazunori Nigorikawa, Yokohamashi, all of Japan

[73] Assignee: Chisso Corporation, Osaka, Japan

[21] Appl. No.: 584,768

[22] Filed: Feb. 29, 1984

[30] Foreign Application Priority Data

Mar. 2, 1983 [JP] Japan .................. 58-34225

[51] Int. Cl.³ .................. C09K 3/34; G02F 1/13; C07C 121/46
[52] U.S. Cl. .................. 252/299.63; 260/464; 350/350 R; 350/350 S
[58] Field of Search .............. 252/299.63; 350/350 R, 350/350 S; 260/464

[56] References Cited

U.S. PATENT DOCUMENTS

| 4,154,697 | 5/1979 | Eidenschink et al. | 252/299.63 |
|---|---|---|---|
| 4,181,625 | 1/1980 | Eidenschink et al. | 252/299.63 |
| 4,229,315 | 10/1980 | Krause et al. | 252/299.63 |
| 4,273,929 | 6/1981 | Boller et al. | 252/299.63 |
| 4,323,504 | 4/1982 | Sethofer | 252/299.61 |
| 4,330,426 | 5/1982 | Eidenschink et al. | 252/299.1 |
| 4,331,552 | 5/1982 | Eidenschink et al. | 252/299.5 |
| 4,405,488 | 9/1983 | Sugimori et al. | 252/299.66 |
| 4,419,263 | 12/1983 | Praefcke et al. | 252/299.63 |
| 4,422,951 | 12/1983 | Sugimori et al. | 252/299.63 |
| 4,432,885 | 2/1984 | Petrzilka et al. | 252/299.62 |
| 4,434,073 | 2/1984 | Sucrow et al. | 252/299.63 |
| 4,439,340 | 3/1984 | Kojima et al. | 252/299.63 |
| 4,472,293 | 9/1984 | Sugimori et al. | 252/299.6 |
| 4,477,369 | 10/1984 | Sugimori et al. | 252/299.6 |

FOREIGN PATENT DOCUMENTS

| 84974 | 8/1983 | European Pat. Off. | 252/299.63 |
|---|---|---|---|
| 90671 | 10/1983 | European Pat. Off. | 252/299.63 |
| 3211601 | 10/1983 | Fed. Rep. of Germany | 252/299.63 |
| 58-99456 | 6/1983 | Japan | 252/299.63 |
| 2111992 | 7/1982 | United Kingdom | 252/299.63 |
| 2092169 | 8/1982 | United Kingdom | 252/299.61 |

OTHER PUBLICATIONS

Billard, J., et al., Mol. Cryst. Liq. Cryst., vol. 41 (Lett.), pp. 217–222 (1978).
Gray, G. W., Mol. Cryst. Liq. Cryst., vol. 63, pp. 3–18 (1981).
Demus, D., et al., Flüssige Kristalle in Tabellen, Veb Deutscher Verlag, Leipzig, p. 34 (1974).

Primary Examiner—Teddy S. Gron
Attorney, Agent, or Firm—Fred Philpitt

[57] ABSTRACT

A liquid crystal substance having a high nematic-clearing point and a broad nematic temperature range and yet a low viscosity, and a composition containing the same, are provided, which substance is 4-unsubstituted or substituted-4"-cyano-trans,trans,trans-tercyclohexanes expressed by the general formula

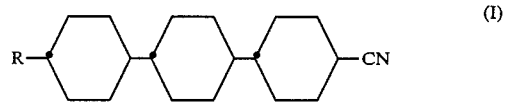

(I)

wherein R represents hydrogen atom or an alkyl group of 1 to 10 carbon atoms.

6 Claims, No Drawings

4-UNSUBSTITUTED OR SUBSTITUTED-4 CYANOTERCYCLOHEXANE DERIVATIVES

BACKGROUND OF THE INVENTION

1. Field of the Invention

This invention relates to new liquid crystal substances which exhibit a liquid crystal phase up to high temperatures and have a positive dielectric anistoropy, and liquid crystal compositions containing the same.

2. Description of the Prior Art

Display elements using liquid crystals have come to be widely used for watches, desk calculators, etc. Such liquid crystal display elements utilize optical anisotropy and dielectric anisotropy of liquid crystal substances, and their liquid crystal phases include nematic liquid crystal phase, smectic liquid crystal phase and cholesteric liquid crystal phase, and those utilizing nematic liquid crystals among them have been most broadly employed for practical uses. Further, liquid crystal display elements include those of TN type (twisted nematic type), DS type (dynamic scattering type), guest-host type, DAP type, etc. and properties required for liquid crystal substances used therefor are varied. At any rate, however, as liquid crystal substances used for these display elements, those which exhibit a liquid crystal phase within as broad a range as possible in the neutral world have been desired. However, no single compounds satisfying such a requirement have been found to date, and it is the present status that liquid crystal compositions which are practically usable for the present have been obtained by mixing together several kinds of liquid crystal compounds or non-liquid crystal compounds. Further, these substances, of course, must be stable to moisture, heat, air, etc., and moreover, it has been desired for the substances that the threshold voltage and saturation voltage required for driving the display elements be as low as possible and the viscosity be as low as possible for making the response speed higher. As a compound which satisfies such requirements to a certain extent, a compound expressed by the formula

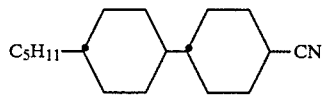

(m.p.: 62° C., c.p. (clearing point): 85° C.) is disclosed in U.S. Pat. No. 4,181,625. However, the recent technical advance of liquid crystal display elements is remarkable, and liquid crystal cells operated within a broad temperature range between still lower ones and still higher ones have been required. Further, for broadening the liquid crystal temperature range toward the higher temperatures, it is necessary to employ a high melting liquid crystal substance as a component, but such a high melting liquid crystal substance generally has a high viscosity and accordingly a liquid crystal composition containing it also has a high viscosity; hence there has been a tendency that the response speed of liquid crystal display elements as usable up to e.g. 80° C., particularly that at lower temperatures, becomes notably slow.

The present inventors have made various studies on liquid crystal compounds meeting the above requirements and as a result have found liquid crystal substances having a high nematic-clearing point (hereinafter abbreviated to N-I point) and a broad nematic temperature range and yet a low viscosity.

SUMMARY OF THE INVENTION

The present invention resides in 4-unsubstituted or substituted-4"-cyano-trans,trans,trans-tercyclohexanes expressed by the general formula

wherein R represents hydrogen atom or an alkyl group of 1 to 10 carbon atoms, and liquid crystal compositions containing the same.

DETAILED DESCRIPTION OF THE INVENTION

Compounds of the present invention have high clearing points. For example, one of the compounds of the present invention, 4-propyl-4"-cyano-trans,trans,trans-tercyclohexane exhibits a liquid crystal phase within a temperature range as broad as a crystalline-smectic point (hereinafter abbreviated to C-Sm point) of 96.0° C., a smectic-nematic point (hereinafter abbreviated to Sm-N point) of 209.5° C. and a N-I point of 244.2° C., and when it is added as one component of liquid crystal compositions, it is possible to raise their cleaning points without any increases in their viscosities. Further the compounds of the present invention have dielectric anisotropy values of about +1, but the threshold voltage and saturation voltage values of the liquid crystal compositions are not changed so much. Further, the compounds have good stabilities to moisture, heat, light, etc. Furthermore, the compounds of the present invention have optical anisotropy values Δn as small as about 0.08; hence they are applicable to cells for display utilizing the above properties.

Next, preparation of the compounds of the present invention will be described. First, a 4-[trans-4'-(trans-4"-substituted cyclohexyl)cyclohexyl]benzoic acid (I) is reduced by metallic sodium in isoamyl alcohol to obtain a 4-substituted-trans,trans,trans-tercyclohexane-4"-carboxylic acid (II), which is then converted with thionyl chloride into an acid chloride (III), which is then reacted with ammonia to obtain an amide (IV), which is subjected to dehydration reaction with thionyl chloride to obtain an objective 4-unsubstituted or substituted-4"-cyano-trans,trans,trans-tercyclohexane (V).

The foregoing is illustrated by chemical equatons as follows:

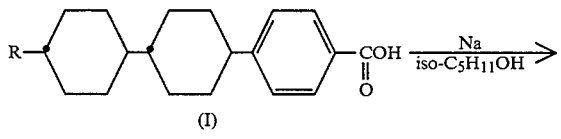

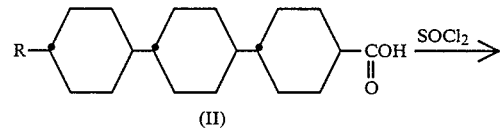

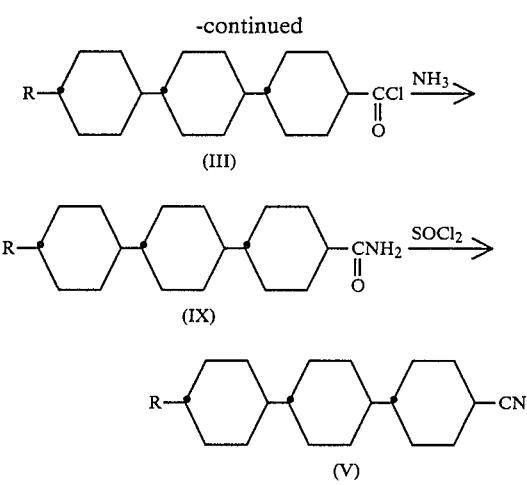

(wherein R is as defined above).

The present invention will be described in more detail by way of Examples.

EXAMPLE 1

Preparation of 4-propyl-4″-cyano-trans,trans,trans-tercyclohexane (1) Preparation of 4-propyl-trans,trans,trans-tercyclohexane-4″-carboxylic acid 4-[Trans-4′-(trans-4″-propylcyclohexyl)cyclohexyl]-benzoic acid (I) (10 g) together with isoamyl alcohol (2,500 ml) were agitated and heated up to 90° C., followed by adding metallic Na (30 g), vigorously reacting them, continuing reflux for 3 hours, and then further adding metallic Na (120 g). The reaction liquid gradually became uniform. After completion of the reaction, the liquid was allowed to cool down to 100° C., followed by distilling off isoamyl alcohol while adding water, adding water (2,000 ml) and then 6N hydrochloric acid (2 l) to completely acidify the liquid, filtering deposited precipitate, washing it with water and recrystallizing from acetic acid to obtain 4-propyl-trans,trans,-trans-tercyclohexane-4″-carboxylic acid (II) (yield: 6.3 g, 63%), which exhibited liquid crystalline properties. C-S point: about 170° C. S-N point: 282° C. N-I point: 290°–300° C. (decomposition).

(2) Cyanogenation

4-Propyl-trans,trans,trans-tercyclohexane-4″-carboxylic acid (II) (5 g) prepared in the above item (1), together with thionyl chloride (30 ml) were heated to 80° C. The reaction liquid became uniform in 2 hours, followed by continuing reaction further for 1.5 hour, distilling off excess thionyl chloride under reduced pressure, adding a remaining oily substance which was an acid chloride to conc. aqueous ammonia (100 ml) with vigorous stirring, further stirring for one hour, filtering the resulting precipitate, air-drying the solids, placing the total amount thereof in a flask and heating them together with thionyl chloride (100 ml) under reflux. The system became almost uniform in 4–5 hours. Excess thionyl chloride was then distilled off under reduced pressure, followed by dissolving a remaining oily substance in toluene (100 ml), three times washing the toluene layer with 2N-NaOH, washing with water till the washing water become neutral, drying with anhydrous sodium sulfate, passing through a column of active alumina, concentrating the resulting elute and twice recrystallizing a remaining oily substance from ethanol to obtain the objective 4-propyl-4″-cyano-trans,trans,trans-tercyclohexane (V). Yield: 1.6 g (34%). C-Sm point: 96.0° C. Sm-N point: 209.5° C. N-I point: 244.2° C. The fact that this product was the objective compound was confirmed by infrared absorption spectra and NMR.

EXAMPLE 2

(Use example)

A liquid crystal composition consisting of
trans-4-propyl-(4′-cyanophenyl)cyclohexane,
  28% by weight,
trans-4-pentyl-(4′-cyanophenyl)cyclohexane,
  42% by weight,
trans-4-heptyl-(4′-cyanophenyl)cyclohexane,
  30% by weight,
has a N-I point of 52° C. This liquid crystal composition was sealed in a TN cell (a twisted nematic cell) of 10 μm thick. The resulting cell exhibited a threshold voltage of 1.53 V, a saturation voltage of 2.12 V, a viscosity at 20° C. of 23 cp and an optical anisotropy value of 0.120.

To this liquid crystal composition (90 parts by weight) was added 4-propyl-4″-cyano-trans,trans,trans-tercyclohexane (10 parts by weight) prepared in Example 1. The resulting liquid crystal composition had a N-I point of 65° C. The threshold voltage and saturation voltage as measured in the same manner as above were 1.55 V and 2.14 V, respectively. Viscosity at 20° C.: 25 cp. The optical anisotropy value was 0.110, that is, somewhat lowered.

What we claim is:

1. 4-unsubstituted or substituted-4″-cyano-trans,-trans,trans-tercyclohexanes having the general formula

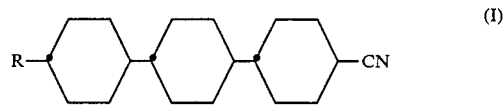

wherein R represents hydrogen atom or an alkyl group of 1 to 10 carbon atoms.

2. A liquid crystal composition comprising a mixture of compounds, at least one of which is a 4-unsubstituted or substituted-4″-cyano-trans,trans,trans-tercyclohexane having the formula

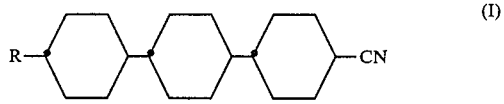

wherein R represents hydrogen atom or an alkyl group of 1 to 10 carbon atoms.

3. A liquid crystal display cell containing a liquid crystal composition comprising a mixture of compounds, at least one of which is a compound as set forth in claim 1.

4. A compound according to claim 1 wherein the alkyl group is propyl.

5. A composition according to claim 2 wherein said alkyl group is propyl.

6. A cell according to claim 5 wherein said at least one compound is 4-propyl-4″-cyano-trans,trans,trans-tercyclohexane.

* * * * *